United States Patent [19]

Hanifl et al.

[11] Patent Number: 4,804,377
[45] Date of Patent: Feb. 14, 1989

[54] URINE COLLECTOR

[75] Inventors: Paul H. Hanifl, Barrington; John J. Newton, Jr., Palatine, both of Ill.

[73] Assignee: Sage Products, Inc., Cary, Ill.

[21] Appl. No.: 82,084

[22] Filed: Aug. 5, 1987

[51] Int. Cl.$^4$ .................................................. A61F 5/44
[52] U.S. Cl. ..................................... 604/352; 128/767; 4/144.2; 4/144.3
[58] Field of Search ............... 604/332, 329, 331, 346, 604/349; 4/144.2, 144.1, 144.3, 144.4, 454, 114.1, 450, 452

[56] References Cited

U.S. PATENT DOCUMENTS

| | | | |
|---|---|---|---|
| 3,200,415 | 8/1965 | Breece, Jr. | 4/144.3 X |
| 3,292,626 | 12/1966 | Schneider | 604/352 X |
| 3,295,145 | 1/1967 | Ericson | 4/144.3 |
| 3,366,116 | 1/1968 | Huck | 604/352 X |
| 3,403,410 | 10/1968 | Benzel et al. | 4/144.2 |
| 3,406,690 | 10/1968 | Igel et al. | 128/767 |
| 3,523,537 | 8/1970 | Hill | 604/352 X |
| 4,309,779 | 1/1982 | Knight | 4/144.3 |

*Primary Examiner*—Larry Jones
*Attorney, Agent, or Firm*—Lee & Smith

[57] ABSTRACT

A urine collector of the type having a flexible collection bag and an adhesively-faced attachment member joined to the bag and which is adapted for attachment to the uro-genital area of an infant or small child. The attachment member is fabricated from a flexible, preformed material such as a foamed plastic and has a barrier formed therein having a raised, curved bulge which is shaped to span the perineum of an infant. A rear recess is formed in the attachment member behind the bulge in order to aid application of the collector to an infant. A removable carrier is secured to the adhesive face of the attachment member to protect the adhesive coating and retain the shape of the attachment member. The carrier is removed before use of the urine collector.

11 Claims, 2 Drawing Sheets

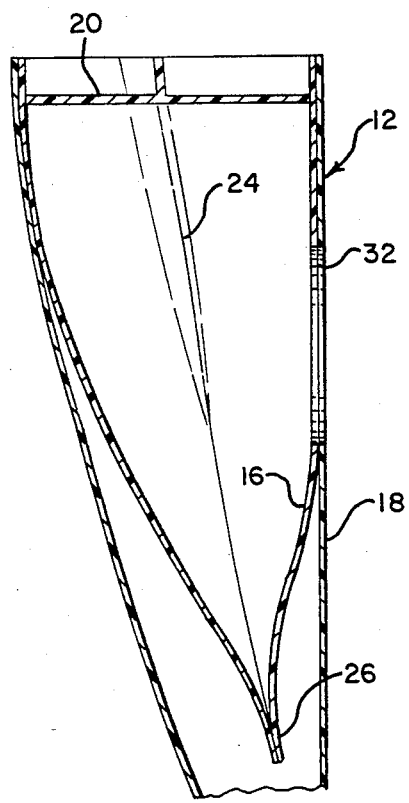
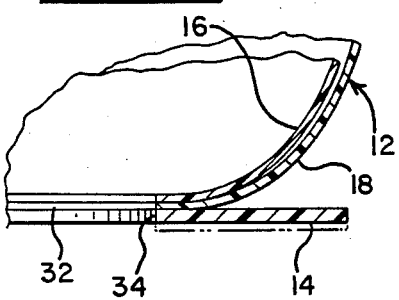
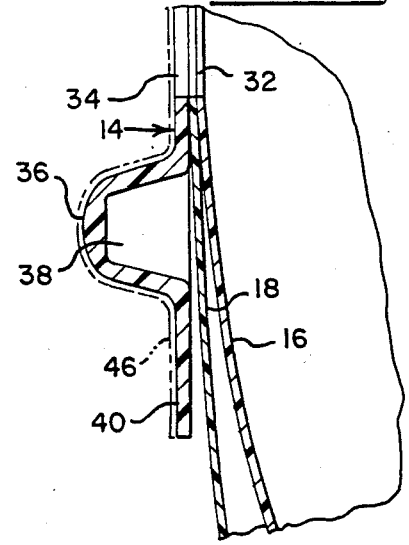
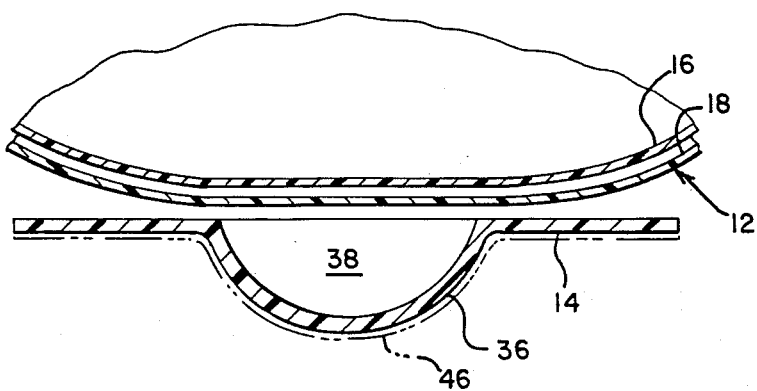

URINE COLLECTOR

BACKGROUND OF THE INVENTION

This invention relates to urine collectors having a flexible collection bag and an adhesively-faced attachment member joined to the bag which is used to affix the collector to the individual utilizing the collector, typically an infant or small child. The invention pertains particularly to an improved collector which provides ease of application and a proper barrier in the perineal area of an infant to block migration of fecal matter and possible contamination of the collected urine specimen.

Many urine collectors have been developed for collection of urine samples from infants. Perhaps the most common currently in use is the urine collector described in Huck U.S. Pat. No. 3,366,116. The urine collector of this patent has a plastic bag for urine collection and an adhesively-faced application material which, because of a vertical fold or pinch, is supposed to form a dam which is intended to eliminate leakage in the lower perineal area. In practice, however, it has been found that unless application is very precise, leakage is not eliminated.

Other urine collection devices have been developed. For example, U.S. Pat. No. 3,523,537 discloses a urine collector which is adhesively attached to an infant, and which also includes a "semi-stiff" plastic separator to separate the walls of the flexible collection bag and properly accommodate the uro-genital area of an infant. No dam or barrier in the perineal area is provided. A similar device, without a plastic separator, is illustrated in U.S. Pat. No. 3,292,626. Again, the device of this patent omits any dam or barrier in the perineal area. Still other urine collectors are found in U.S. Pat. Nos. 2,877,769; 3,077,883; 3,200,415 and 3,340,876, all of which have no dam or barrier in the perineum.

SUMMARY OF THE INVENTION

The invention provides an improved urine collector of the type having a collection bag with a urine inlet and an adhesively-faced attachment member which is joined to the bag at the urine inlet. In accordance with the invention, the attachment member comprises a flexible, preformed material having a central opening aligned with the urine inlet, with the attachment member being substantially planar and the collection bag being secured to the attachment member at the central opening. A barrier is formed in the attachment member adjacent the central opening and includes a raised, curved bulge shaped to span the perineum of an infant.

Preferably, the bulge has a substantially constant wall thickness, therefore forming a rear recess to aid in proper application of the attachment member to an infant. The bulge extends across the attachment member for approximately the width of the central opening. The attachment member is preferably formed of a soft, pliable, cellular plastic foam which, although pliable, has a structural integrity of its own, and has a "memory" so that if the attachment member is deformed, it will usually return to its preformed state.

A removable carrier is secured to the adhesive face of the attachment member. The carrier is semi-rigid and conforms to the attachment member and the bulge. Thin plastics, such as polystyrene, are suitable for the carrier, and can be readily separated from the adhesive face of the attachment member.

BRIEF DESCRIPTION OF THE DRAWINGS

The invention is described in greater detail in the following description of an example embodying the best mode of the invention, taken in conjunction with the drawing figures, in which:

FIG. 3 is an enlarged cross-sectional view taken along lines 3—3 of FIG. 2, with unnecessary detail broken away, illustrating the nature to the inner and outer urine collection bags, and with the attachment member removed, FIG. 4 is an enlarged cross-sectional view taken along lines 4—4 of FIG. 2, FIG. 5 is an enlarged cross-sectional view taken along lines 5—5 of FIG. 4, and illustrating the removed carrier in phantom, and FIG. 6 is an enlarged cross-sectional view taken along lines 6—6 of FIG. 2, also having the removed carrier illustrated in phantom.

DESCRIPTION OF AN EXAMPLE EMBODYING THE BEST MODE OF THE INVENTION

Figures 1, 2:
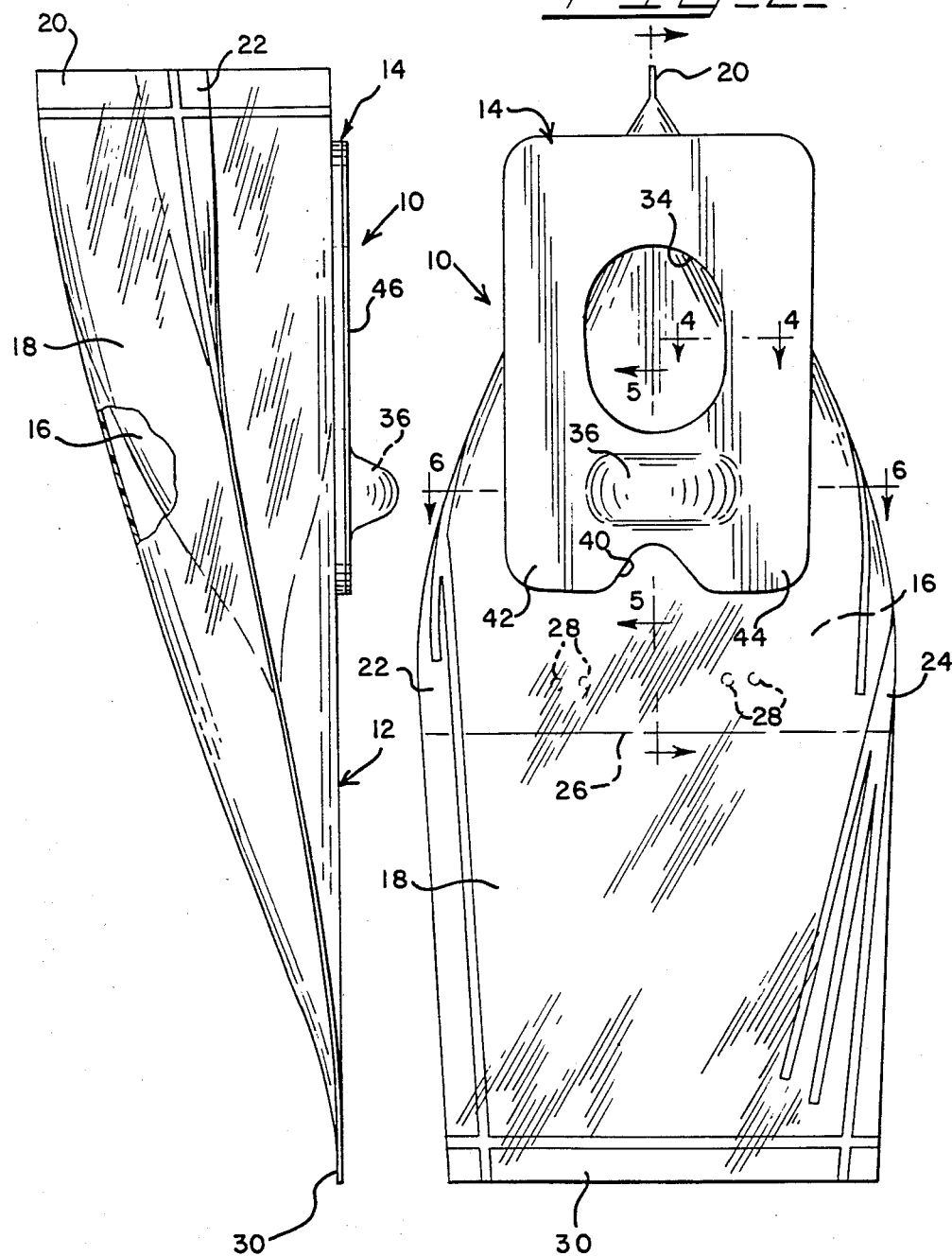
FIG. 1 is a side elevational view of a urine collector according to the invention illustrating the carrier in place on the adhesive face of the attachment member.
FIG. 2 is a front elevational view of the urine collector illustrated in FIG. 1, with the carrier removed.

A urine collector according to the invention is designated at 10 in the drawing figures. The urine collector is composed of two basic elements, a pair of partially coextensive collection bags 12 and an attachment pad or member 14 permanently secured to the bags 12.

The bags 12 are composed of an inner bag 16 and an outer bag 18. The bags 16 and 18 are joined at a common top seam 20 and opposite shared side seams 22 and 24. The inner bag 16 terminates at an outlet 26 open to the interior of the outer bag 18. The inner bag 16 may be fully open at the outlet 26, or may have periodic seals 28 to gather and substantially close the outlet 26. The outer bag 18 includes a bottom seam 30 and may be provided with means (not illustrated) for expelling its contents, such as a sealed hole or a tear-initiation cut in one of the seams 22 or 24.

The bags 16 and 18 include a common inlet 32 (FIG. 3) and are joined to the rear of the attachment member 14 at a central opening 34 therein. The bags 16 and 18 may be heat sealed to the attachment member 14, or may be otherwise affixed as desired.

In addition to the central opening 34, the attachment member 14 also includes a raised, curved bulge 36 situated beneath the central opening 34 and extending across the attachment member 14 for approximately width of the opening 34. The bulge 36 is shaped to span the perineum of an infant. As best shown in FIG. 5, the bulge 36 has a substantially constant wall thickness, forming a rear recess 38 accessable by a nurse, physician or other person applying the collector 10 and therefore aiding the application of the attachment member 14 to the infant.

To also aid in its application, the attachment member 14 includes a curved notch 40 along its lower edge which forms a pair of spaced tabs 42 and 44 at the lower margin of the barrier means 14. The notch 40 also facilitates easy access to the rear recess 38.

It is preferred that the attachment member 14 have an adhesive face (not illustrated in detail) for application to the infant. To protect the adhesive face of the attachment member 14, a semi-rigid carrier 46 is provided, substantially coextensive with the extent of the attachment member 14. Not only does the carrier 46 protect the adhesive face of the attachment member 14, but also it is preferred that the carrier member 46 be sufficiently rigid in order to protect the contours of the attachment member 14, particularly the bulge 36. When the collector 10 is to be used, the carrier 46 is removed and discarded.

Preferably, the attachment member 14 and carrier 46 are formed together. As indicated above, the attachment member 14 is made from a plastic foam, while the carrier member 46 is formed of a thin, semi-rigid plastic, such as polystyrene. The material for both the attachment member 14 and carrier 46 are formed in large sheets, and after an adhesive face has been applied to the material for the attachment member 14, that material and the material for the carrier 46 are joined. Thereafter, the central opening 34 and the barrier 36 are formed, and the completed combination of the attachment member 14 and the carrier 46 are cut to the shape shown in the drawing figures. Finally, the bags 16 and 18 are heat sealed to the rear of the attachment member 14 and the inlet 32 is formed coextensive with the opening 34. The formation of the attachment member 14, carrier 46 and bags 16 and 18 can proceed in accordance with well-known cutting and sealing processes which are therefore not described in further detail.

ACHIEVEMENTS

The invention provides a significant advance in urine collection devices. The barrier 36, being formed as a raised, curved bulge in the attachment member 14, and having the rear reces 38, permits ready application to an infant and proper damming of the perineal area to assure that fecal matter does not inadvertently contaminate the contents of the urine collector 10. The foam or similar material of the attachment member 14 is soft, comfortable, and allows the infant to move with the attachment member 14 continuing to conform to the contours of the infant's body. The foam material of the attachment member 14 has sufficient structural integrity and a "memory" so that if it is deformed, it will return to its normal, preformed state.

The carrier 46 protects the adhesive face of the attachment member 14 and also helps retain the shape of the bulge 36. Because both the attachment member 14 and carrier 46 are preferably formed from plastic materials, their fabrication is simple and easy using common, well-known methods.

Various changes can be made to the invention without departing from the spirit thereof or scope of the following claims.

What is claimed is:

1. In a urine collector having a collection bag with a urine inlet and an adhesively-faced attachment member joined to the bag at the urine inlet, the improvement comprising.
   a. the attachment member comprising a flexible, preformed material having a central opening aligned with said inlet, said attachment member having a substantially planar attachment surface and said collection bag being secured to said attachment member at said opening, and
   b. a barrier formed in the attachment member, said barrier being positioned adjacent said opening and including a raised bulge extending above said attachment surface and shaped to span the perineum of an infant.

2. A urine collector according to claim 1 in which said bulge has a substantially constant wall thickness, forming a rear recess means to aid application of said attachment member.

3. A urine collector according to claim 1 including a removable carrier secured to the adhesive face of said attachment member.

4. A urine collector according to claim 3 in which said carrier is semi-rigid and conforms to said attachment member and said bulge.

5. A urine collector according to claim 1 in which said bulge is curved and extends across said attachment member for the width of said opening.

6. A urine collector according to claim 1 in which said collection bag comprises a double-bag configuration having a sealed outer bag and an inner bag open to the interior of said outer bag.

7. A urine collector according to claim 6 in which said inner bag coextends with a portion of said outer bag.

8. A urine collector according to claim 1 in which said attachment member comprises a soft, pliable, cellular plastic foam.

9. A method of forming a urine collector, comprising the steps of
   a. forming a composite structure comprising a flexible, adhesively-faced attachment member having a substantially planar attachment surface and a semi-rigid, removable carrier secured to the attachment surface of said attachment member,
   b. forming a central opening and a barrier member in said composite structure, said barrier member being located adjacent said opening and having a raised, curved bulge extending above said attachment surface and shaped to span the perineum of an infant, and
   c. attaching a collection bag to said attachment member at said central opening.

10. A method according to claim 9 in which method step "c" includes the steps of heat sealing said collection bag to said attachment member, and forming a urine inlet in said collection bag coextensive with said central opening.

11. A urine collector formed by the method of claim 9.

* * * * *